United States Patent [19]
Winkler

[11] Patent Number: 5,269,798
[45] Date of Patent: Dec. 14, 1993

[54] SURGICAL CUTTING INSTRUMENT WITH MOVABLE, INNER AND OUTER TUBULAR MEMBERS

[75] Inventor: Rance A. Winkler, Largo, Fla.

[73] Assignee: Linvatec Corporation, Largo, Fla.

[21] Appl. No.: 836,961

[22] Filed: Feb. 19, 1992

[51] Int. Cl.$^5$ ............................................. A61B 17/32
[52] U.S. Cl. .................................. 606/170; 606/174; 30/345
[58] Field of Search .................. 604/22, 265; 606/170, 606/171, 174; 30/345

[56] References Cited

U.S. PATENT DOCUMENTS

| | | | |
|---|---|---|---|
| 4,335,924 | 6/1982 | McCloskey | 308/72 |
| 4,923,441 | 5/1990 | Shuler | 604/22 |
| 5,135,533 | 8/1992 | Petersen et al. | 30/345 |
| 5,160,318 | 11/1992 | Shuler | 604/22 |

OTHER PUBLICATIONS

Metallorgical Materials & Processes, Elberfeld, Prentice-Hall, Inc, New York pp. 76, 82.
Hardcor, BV, Postbus 65, Beckbergen, Netherlands.

Primary Examiner—Jerome L. Kruter

[57] ABSTRACT

A surgical cutting instrument formed of relatively movable, cooperating, inner and outer elongate tubular members wherein one of the inner and outer tubular members is made of a gall-resistant material providing an elongate bearing surface along substantially the entire length of the surgical cutting instrument to allow the inner and outer tubular members to be mounted with virtually no gap therebetween for precision cutting without wear or abrasion, metal flaking, galling and seizure and while permitting the other of the inner and outer tubular members to be made from 300 Series stainless steel. When the outer member is made from gall-resistant material, the inner member made from 300 Series stainless steel can be provided with an elongate bearing surface therealong formed by surface hardening the inner member or coating the inner member with thin, dense chromium. The outer tubular member can be made of 300 Series stainless steel with the inner tubular member including a distal tip made from gall-resistant material, a body made from 300 Series stainless steel joined to the distal tip and a bearing surface extending along the body. A biocompatible lubricant can be disposed between the inner and outer members to increase wear and galling resistance of the surgical cutting instrument, and a sleeve bearing on the inner tubular member allows the surgical cutting instrument to withstand increased radial or side loads.

28 Claims, 3 Drawing Sheets

SURGICAL CUTTING INSTRUMENT WITH MOVABLE, INNER AND OUTER TUBULAR MEMBERS

BACKGROUND OF THE INVENTION

1. Field of the Invention

The present invention pertains to surgical cutting instruments and, more particularly, to surgical cutting instruments having relatively movable, elongate inner and outer tubular members for cutting tissue, with the inner and outer tubular members being mounted with minimal or no gap or clearance therebetween.

2. Description of the Prior Art have been proposed, and such instruments are usually elongated to permit distal ends of the instruments to be positioned at internal operative sites through one or more portals. Surgical cutting instruments for endoscopic use frequently include relatively movable, cooperating, concentric inner and outer tubular members that are longitudinally elongated such that distal ends of the inner and outer tubular members can be positioned at internal operative sites via the portals while proximal ends of the inner and outer tubular members can be secured, externally of the body, in a handpiece for relatively moving the inner and outer tubular members. The distal end of the outer tubular member is commonly formed with an opening defining a cutting port, or window, to receive bodily tissue, and the distal end of the inner tubular member is formed with a surface, or edge, to engage the tissue through the opening when the inner tubular member is moved relative to the outer tubular member. The surface or edge on the inner tubular member distal end cooperates with the opening in the outer tubular member distal end to shear, abrade or otherwise cut the tissue when the surface is moved adjacent the opening. In many cases, the inner tubular member is rotated in the outer tubular member by a motor disposed in the handpiece and coupled to the proximal end of the inner tubular member with the motor being controlled by switches on the handpiece, the floor, or a console powering the handpiece. The surface or edge on the inner tubular member distal end and the opening in the outer tubular member distal end are typically configured to produce a variety of cutting functions, such as whisker cutting, synovial resection, arthroplasty burring or abrading, side cutting, meniscus cutting, trimming, full radius resection and end cutting, appropriate for diverse types of tissue, such as soft tissue, cartilage and bone. Suction is normally produced through the handpiece and the lumen of the inner tubular member to permit cut tissue to be aspirated from the surgical site through the inner tubular member.

During operation, the surface or edge on the inner tubular member distal end must be accurately positioned and aligned relative to the opening in the outer tubular member distal end to insure a precise cut and optimum cutting efficiency as measured by the force required to rotate the cutting surface. In other words, the inner tubular member cannot be cocked or oriented askew with the longitudinal axis of the surgical cutting instrument when the cutting surface is moved through tissue positioned in the opening. Accordingly, a bearing structure is commonly necessary to maintain exact positioning and alignment of the cutting surface with the opening while allowing the inner tubular member to rotate freely within the outer tubular member; and, in most instances, the bearing structure is disposed at the inner tubular member distal end or at spaced locations along the length of the inner tubular member. Such bearing structure possesses many disadvantages including structural complexity, increased manufacturing cost resulting in a very expensive product that is incompatible with disposability, or single patient use, and reduced reliability and anticipated life due to greater opportunities for malfunction from sticking and obstruction, and a simplified bearing for use in surgical instruments formed of relatively movable, inner and outer tubular members to allow the instruments to safely withstand increased radial or side loads has not been proposed.

Another approach to obtaining accurate alignment and positioning of a movable inner tubular member within an outer tubular member of a surgical instrument involves reducing the gap, or clearance, between the outer diameter surface of the inner tubular member and the inner diameter surface of the outer tubular member such that there is minimal or virtually no gap or clearance between the inner and outer tubular members. By making the outer diameter of the inner tubular member substantially the same as the inner diameter of the outer tubular member, or as close as possible thereto, misalignment of the inner tubular member within the outer tubular member in response to the cutting action can be avoided. A major drawback to this approach is that it is preferred to construct the inner and outer tubular members of AISI 300 Series stainless steel due to the cost benefits obtained with stainless steel; however, the physical properties of 300 Series stainless steel limit the effectiveness of 300 Series stainless steel as a bearing surface. In particular, surgical instruments having relatively movable, inner and outer tubular members made from 300 Series stainless steel are prone to failure due to the relative softness of 300 Series stainless steel and the surface to surface contact that occurs between the inner and outer tubular members when the gap between the inner and outer members is very small. Additionally, great frictional heat is generated at areas of contact between the inner and outer tubular members due to the relatively high coefficient of friction for 300 Series stainless steel. The frictional heat generated during operation of a surgical cutting instrument can be significant as the inner tubular member can rotate within the outer tubular member at very high speeds, i.e. 2500 RPM and greater. When inner and outer tubular members made from 300 Series stainless steel bear on and contact each other, considerable frictional heat is produced at the contact areas causing the inner tubular member to thermally expand. As the inner tubular member expands, areas of contact between the inner and outer tubular members increase producing greater friction and wear due to abrasion, particularly at the distal end of the instrument where heat can become concentrated. Eventually, the grain structure of the stainless steel inner and outer tubular members begins to "flake", and increased abrasion and frictional heat occurs due to metal flaking. Further expansion of the inner tubular member creates localized hot spots at the contact areas, and welding of the inner and outer tubular members at the hot spots occurs. As the inner tubular member continues to rotate within the outer tubular member, additional weld junctions are produced eventually resulting in galling, wherein the weld junctions sever or tear creating a build-up of metal on one of the tubular members that promotes abrasion and thermal expansion until the inner tubular member has expanded further than the gap between it and the outer tubular member and the instrument seizes. Biocompatible lubricants for effectively reducing abrasion between relatively movable inner and outer tubular members of surgical cutting instruments have not previously been recognized or proposed; and, accordingly, wear or abrasion, metal flaking, galling and catastrophic seizure in surgical instruments having relatively movable inner and outer tubular members made from stainless steel have commonly been avoided by increasing the gap or clearance between the inner and outer tubular members such that contact between the inner and outer tubular members is prevented or greatly minimized. Although increasing the clearance between the inner and outer tubular members can prolong the life of surgical cutting instruments, cutting quality and efficiency are drastically reduced, and the instruments perform poorly in surgical procedures requiring precision cutting. A relatively large gap or clearance between the inner and outer tubular members permits misalignment of the inner tubular member relative to the longitudinal axis of the surgical instrument in response to the cutting action. Accordingly, the cutting surface on the inner tubular member will not be properly aligned with the opening in the outer tubular member resulting in cutting inaccuracies and inefficiencies. Furthermore, a relatively large gap between the distal end of the inner tubular member and the distal end of the outer tubular member allows tissue in the opening to become caught between the inner and outer tubular members during operation; and, in many instances, tissue can become wrapped around the inner tubular member as it rotates within the outer tubular member thusly compromising the cutting procedure. Moreover, elongated surgical instruments are typically subjected to considerable thrust and radial loads during operation, particularly at the distal ends of the inner and outer members, and inner and outer tubular members made from 300 Series stainless steel cannot withstand high thrust and radial loads without experiencing deformation and damage.

A surgical cutting instrument having an inner tubular member coated with titanium nitride and movably mounted in an outer tubular member has been proposed in U.S. Pat. No. 4,923,441 to Shuler. The titanium nitride coating extends continuously along the outer diameter of the inner tubular member from a proximal end to a distal end including a cutting surface at the distal end. Forming one of the inner and outer members of gall-resistant material to provide superior bearing and strength characteristics has not been recognized. Furthermore, the use of a chromium coating or a surface hardened case as a bearing surface on the outer diameter of a stainless steel inner tubular member has not been recognized or proposed.

Chromium coatings have been utilized in industrial applications on metal surfaces, and prior uses of chromium coatings are illustrated in U.S. Pat. Nos. 1,753,773 to Champion; 1,809,412 to DeVore; 3,063,763 to Zubrisky; 4,335,924 to McCloskey; and 4,692,080 to Hyner et al. Chromium coatings have not been utilized as a bearing surface on an inner tubular member of a surgical cutting instrument formed of relatively movable, elongate inner and outer tubular members to allow the outer diameter of the inner tubular member to be the same as, or as close as possible to, the inner diameter of the outer tubular member to eliminate abrasion or wear, metal flaking and galling or seizure in the surgical instrument and to permit the inner and outer tubular members to withstand increased thrust and radial roads while being made from 300 Series stainless steel.

Gall-resistant materials have also been employed in industrial applications, and illustrative gall-resistant stainless steel alloys include Nitronic 60, manufactured by Armco Steel Corporation and disclosed in U.S. Pat. No. 3,912,503 to Schumacher et al, Waukesha 88, made by Waukesha Foundry, Inc. and Gall-Tough Stainless, manufactured by Carpenter Technology Corporation. It has not been recognized to form an inner or outer tubular member of a surgical cutting instrument including relatively movable, elongate inner and outer tubular members from gall-resistant material to allow the inner tubular member to be mounted in the outer tubular member with little or no gap therebetween while permitting the surgical instrument to resist wear and abrasion, metal flaking, galling and seizure and to withstand high thrust and radial loads.

Surface hardening of stainless steel has also been employed in industrial applications to increase the operational life of stainless steel components; however, it has not been recognized to surface harden an outer diameter surface of an inner tubular member of a surgical cutting instrument formed of relatively movable, inner and outer tubular members to provide a bearing surface along the inner tubular member allowing the inner tubular member to be mounted within the outer tubular member with little or no gap therebetween while avoiding wear or abrasion, galling and seizure of the surgical instrument and while allowing the surgical instrument to withstand high thrust and radial loads.

SUMMARY OF THE INVENTION

Accordingly, it is a primary object of the present invention to overcome the above-mentioned disadvantages of prior art surgical cutting instruments formed of relatively movable, elongate, inner and outer tubular members.

Another object of the present invention is to provide a surgical cutting instrument having relatively movable, elongate inner and outer tubular members wherein one of the inner and outer tubular members is made from gall-resistant material to enable the inner and outer tubular members to be disposed with little or no gap therebetween while avoiding abrasion or wear, metal flaking, galling and seizure of the surgical instrument and while allowing the surgical instrument to withstand high thrust and radial loads.

A further object of the present invention is to provide a surgical cutting instrument formed of relatively movable, elongate inner and outer tubular members mounted with little or no gap or clearance therebetween and wherein the inner tubular member has a distal tip made from gall-resistant material, a cutting edge on the distal tip and an elongate bearing surface extending longitudinally from a proximal end to the distal tip to allow relative movement between the inner and outer tubular members without abrasion or wear, metal flaking, galling and seizure of the surgical instrument and while enabling the inner and outer tubular members to withstand relatively high thrust and radial loads.

It is also an object of the present invention to provide an inner tubular member of a surgical cutting instrument formed of relatively movable, inner and outer tubular members with a chromium coating as a bearing surface along the inner member to enable the inner member to be disposed within the outer member with little or no gap therebetween while avoiding abrasion or wear, metal flaking, galling and seizure of the surgical instrument.

Yet another object of the present invention is to provide an inner tubular member of a surgical cutting instrument formed of relatively movable, inner and outer tubular members with a surface hardened outer case as a bearing surface along the inner member to enable the inner member to be disposed within the outer member with little or no gap or clearance therebetween while avoiding abrasion or wear, metal flaking, galling and seizure of the surgical instrument.

Additionally, it is an object of the present invention to provide a biocompatible lubricant between relatively movable, inner and outer tubular members of a surgical cutting instrument to avoid wear or abrasion, metal flaking, galling and seizure of the surgical instrument while permitting the inner member to be disposed within the outer member with virtually no gap therebetween.

A still further object of the present invention is to provide a simplified bearing between relatively movable, inner and outer tubular members of a surgical instrument to allow the surgical instrument to safely withstand increased radial or side loads.

Some of the advantages of the present invention are that expensive and complex bearing structure is eliminated, the surgical instrument can be simply and economically manufactured for single patient use, life of the surgical instrument is prolonged without sacrificing cutting quality and efficiency, the surgical instrument is able to withstand relatively high temperatures without deformation or damage and the tendency for tissue to become caught between the inner and outer tubular members is avoided.

These and other objects, attributes and advantages are obtained with the present invention as characterized in a surgical cutting instrument including an outer tubular member having a distal end and an opening at the distal end for receiving anatomical tissue and an inner tubular member having a distal end and a cutting surface at the distal end for engaging anatomical tissue, with the inner tubular member being disposed within the outer tubular member to permit relative movement between the inner and outer tubular members to position the cutting surface to engage and cut tissue through the opening. One of the inner and outer tubular members is made from a gall-resistant material to form an elongate bearing surface along substantially the entire length of the surgical cutting instrument allowing the inner diameter of the outer tubular member to be the same, or substantially the same, as the outer diameter of the inner tubular member to permit the inner and outer tubular members to be mounted for relative movement with little or no gap therebetween while avoiding wear or abrasion, metal flaking, galling and seizure of the surgical instrument and while enabling the surgical instrument to withstand relatively high radial and thrust loads. When the outer tubular member is made from gall-resistant material, the inner tubular member can be made of 300 Series stainless steel; and, additionally, a bearing surface can be fixed and secured on the outer diameter of the inner tubular member to further enhance the wear and gall-resistance of the surgical cutting instrument. The bearing surface on the outer diameter of the inner tubular member can include an outer case formed by surface hardening the inner tubular member or a coating of chromium formed on the inner tubular member by electrodeposition. The present invention is further characterized in a surgical cutting instrument formed of relatively movable, cooperating, inner and outer elongate tubular members wherein the outer tubular member is made from 300 Series stainless steel and the inner tubular member includes a body made from 300 Series stainless steel, a distal tip of gall-resistant material joined to the body and including a cutting surface thereon and a bearing surface secured on the body. The bearing surface can include a surface hardened outer case or a coating of chromium that extends substantially the entire length of the body from the distal tip to a proximal end of the inner tubular member. A sleeve bearing formed of a length of thin-walled tubing can be heat-shrunk on the inner tubular member to enable the surgical cutting instrument to withstand increased radial or side loads. The present invention is further characterized in a surgical cutting instrument formed of relatively movable, cooperating, inner and outer tubular members wherein an elongate bearing surface is provided on one of the inner and outer tubular members extending substantially the entire length of the surgical instrument and a biocompatible lubricant is disposed between the bearing surface and the other of the inner and outer tubular members to allow the inner and outer tubular members to be mounted with virtually no gap therebetween for efficient, precision cutting without wear or abrasion, metal flaking, galling and seizure of the surgical cutting instrument.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENTS

Figure 1:
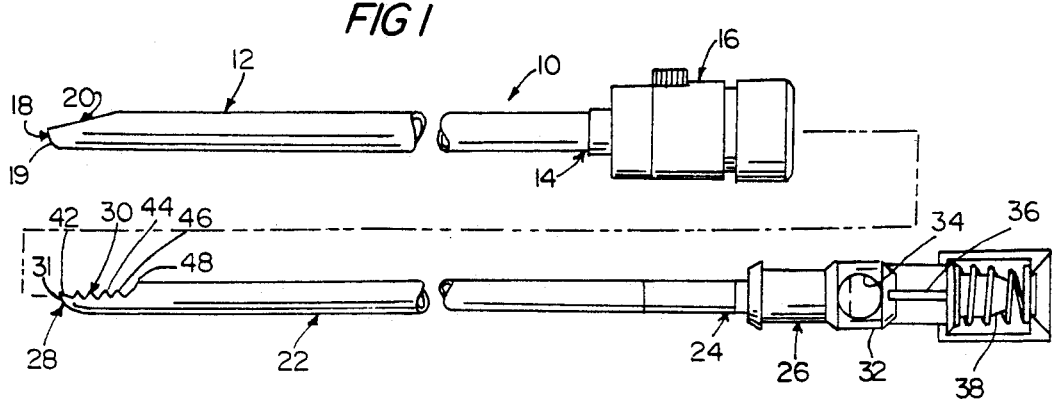
FIG. 1 is an exploded, side view of a surgical cutting instrument according to the present invention.
Figure 2:
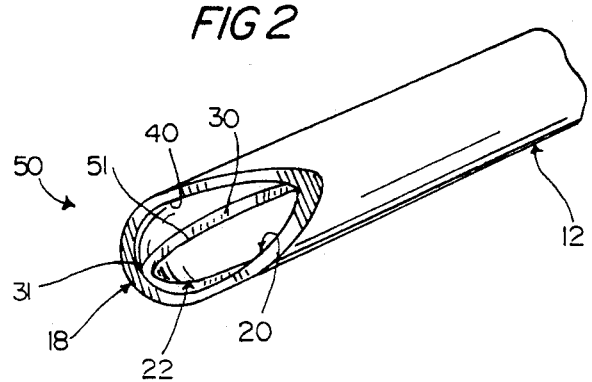
FIG. 2 is a broken, perspective view of a distal end of a modification of a surgical cutting instrument according to the present invention.

As shown in FIGS. 1 and 2, a surgical cutting instrument 10 according to the present invention includes an elongate outer tubular member 12 having a proximal end 14 secured to a plastic hub 16 and a distal end 18 terminating at an end wall 19 and having an opening 20 therein forming a cutting port, or window, for receiving anatomical tissue through the opening 20. An elongate inner tubular member 22 is movably, concentrically disposed in the outer tubular member 12 and has a proximal end 24 secured to a hub 26 and a distal end 28 having a cutting surface, or edge, 30 formed thereon for being positioned adjacent the opening 20 to engage tissue in the cutting port. The hub 26 is preferably made of plastic and is configured to be received in an annular recess (not shown) in the hub 16, the hub 16 preferably being made of plastic. The hub 26 includes an enlarged, central barrel 32 having a transverse passage 34 extending therethrough in communication with an axial bore in the hub 26 receiving the proximal end 24 of the inner tubular member 22. Rib 36 extends longitudinally in the proximal direction from the barrel 32, and a driven tang 38 extends longitudinally in the proximal direction from the ribs 36 for coupling to a rotatable, slotted drive shaft (not shown) of an electric motor in a handpiece securing the hubs 16 and 26. The structure of hubs 16 and 26 is described in general terms since the hubs correspond to those utilized in the Concept INTRA-ARC Drive System of Linvatec Incorporated, Concept Division, designed for detachably, concentrically mounting an inner tubular member in an outer tubular member and moving or rotating the inner tubular member within the outer tubular member as manually controlled by switches on the handpiece, the floor or a console supplying power to the handpiece.

The opening 20 in the distal end 18 of the outer tubular member 12 is formed by an angled cut through the cylindrical wall of the outer tubular member, the cut extending through the end wall 19 to produce an edge 40 that is generally oval or elliptical in configuration when viewed from above as shown in FIG. 2. As shown in FIG. 1, the cutting surface 30 on the distal end 28 of the inner tubular member 22 is formed to extend along an end wall 31 and opposing sides of the cylindrical wall of the inner tubular member and includes a leading cutting edge 42 extending along end wall 31 that is arcuate in configuration when viewed from above angularly joined to side cutting edges 44 extending along opposing sides of the cylindrical wall of the inner tubular member. The side cutting edges 44 are defined by a series of triangular shaped cutting teeth 46 extending linearly along the opposing sides of the cylindrical wall of the inner tubular member 22 from the leading cutting edge 42 to chamfered surfaces 48 joining the side cutting edges 44 to a top wall of the inner tubular member 22. The leading cutting edge 42 and the side cutting edges 44 cooperate with the edge 40 on the outer tubular member 12 to cut tissue in the opening 20 in a clean shear cut when the cutting surface 30 is rotated past the edge 40. It will be appreciated that the cutting surface 30 can have any desired configuration, and the edge 40 can have a configuration to cooperate with the configuration of the cutting surface 30 including, but not limited to, the various cutting tip designs of the Concept INTRA-ARC Blade System of Linvatec Incorporated, Concept Division, such as to form trimmers, meniscus cutters, end cutters, side cutters, full radius resectors, synovial resectors, whiskers, open end cutters, arthroplasty burrs, slotted whiskers, tapered burrs, oval burrs, punch forceps and the like. Although the surgical cutting instrument of the present invention is shown and described for use in the Concept INTRA-ARC Drive System, it will be appreciated that the surgical cutting instrument of the present invention can have any desired hub configuration to be utilized with any drive system or handpiece capable of relatively moving concentric, elongate, inner and outer tubular members to engage bodily tissue and aspirate tissue through the lumen of the inner tubular member.

The outer tubular member 12 is made from 300 Series stainless steel in its entirety, and the inner tubular member 22 is made in its entirety from gall-resistant material, preferred gall-resistant materials including gall-resistant, austenitic stainless steel alloys such as Nitronic 60, manufactured by Armco Steel Corporation, Waukesha 88, made by Waukesha Foundry, Inc. and Gall-Tough Stainless, manufactured by Carpenter Technology Corporation. The outer diameter of the inner tubular member 22 is substantially the same as the inner diameter of the outer tubular member 12 such that there is minimal, i.e. 0.00075 inch or less, or no gap or clearance between the inner and outer tubular members.

According to a method of operation for the surgical cutting instrument 10, the inner tubular member 22 is rotated relative to the outer tubular member 12 via the handpiece such that the cutting surface 30 engages bodily tissue positioned in the cutting port or window formed by the opening 20 and cuts the tissue as the cutting surface 30 is moved adjacent the opening with cut tissue being aspirated through the lumen of the inner tubular member 22 to exit the surgical cutting instrument through the handpiece. The inner tubular member 22 being made of gall-resistant material in its entirety allows the inner member to be disposed within the outer tubular member 12 with virtually no gap or clearance therebetween; and, therefore, the cutting surface 30 is maintained in precise alignment with the opening 20 to maximize cutting precision and efficiency. The inner tubular member 22 exhibits superior bearing properties when utilized with the 300 Series stainless steel outer tubular member 12, and the gall-resistant material forms a bearing surface along the entire length of the inner member that reacts effectively with the 300 Series stainless steel outer member to avoid wear or abrasion, metal flaking, galling and seizure of the surgical instrument during operation wherein the inner tubular member can be rotated within the outer tubular member at speeds of 2500 RPM and greater. The inner tubular member 22 disburses heat and eliminates hot spots along the length of the surgical instrument while avoiding concentrations of heat at the distal end. Additionally, the inner tubular member 22 possesses increased strength to withstand significantly greater thrust and radial loads. Accordingly, easier and smoother precision cutting is accomplished with the surgical cutting instrument as accurate alignment of the cutting surface 30 with the opening 20 greatly enhances cutting efficiency and reduces the cutting force and the time required to cut tissue. Moreover, tissue is prevented from becoming caught between the inner and outer members during operation due to there being negligible or no gap between the inner and outer tubular members.

A modification of a surgical cutting instrument according to the present invention is shown in FIG. 2 at 50. The surgical cutting instrument 50 is substantially the same as the surgical cutting instrument 10 and includes outer tubular member 12 made of 300 Series stainless steel and inner tubular member 22 made of gall-resistant material in its entirety; however, the cutting surface 30 for the surgical cutting instrument 50 is flat and not toothed, and extends along end wall 31 and the cylindrical wall of the inner tubular member 22 to define an edge 51 that is generally oval or elliptical in configuration when viewed from above for cooperating with the edge 40 of opening 20 of the outer tubular member 12 to form a full radius resector.

Figure 3:
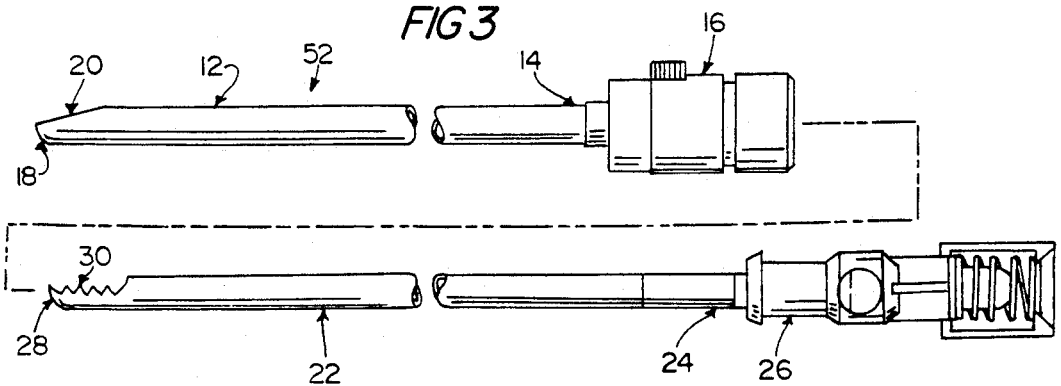
FIG. 3 is an exploded, side view of another modification of a surgical cutting instrument according to the present invention.

Another modification of a surgical cutting instrument according to the present invention is shown in FIG. 3 at 52. The surgical cutting instrument 52 is substantially the same as the surgical cutting instrument 10 and includes an outer elongate tubular member 12 having a distal end 18 with an opening 20 for receiving tissue and a proximal end 14 coupled to the hub 16, and an inner elongate tubular member 22 having a distal end 28 with a cutting surface 30 and a proximal end 24 coupled to the hub 26; however, the outer tubular member 12 for the surgical cutting instrument 52 is made from gall-resistant material in its entirety, and the inner tubular member 22 for the surgical cutting instrument 52 is made from 300 Series stainless steel in its entirety. The gall-resistant material of the outer tubular member 12 forms a bearing surface along the inner diameter surface of the outer member extending the entire length of the surgical cutting instrument for allowing the inner diameter surface of the outer member to engage the outer diameter surface of the inner tubular member 22 without wear or abrasion, metal flaking, galling and seizure and while enabling the surgical instrument to withstand high thrust and radial loads when the inner tubular member is moved within the outer tubular member. It will be appreciated that the cutting surface 30 and the edge 40 of opening 20 for the surgical cutting instrument 52 can have various configurations, including the configuration of FIG. 2, to provide diverse types of cutting actions in various, diverse types of anatomical tissue.

Figure 4:
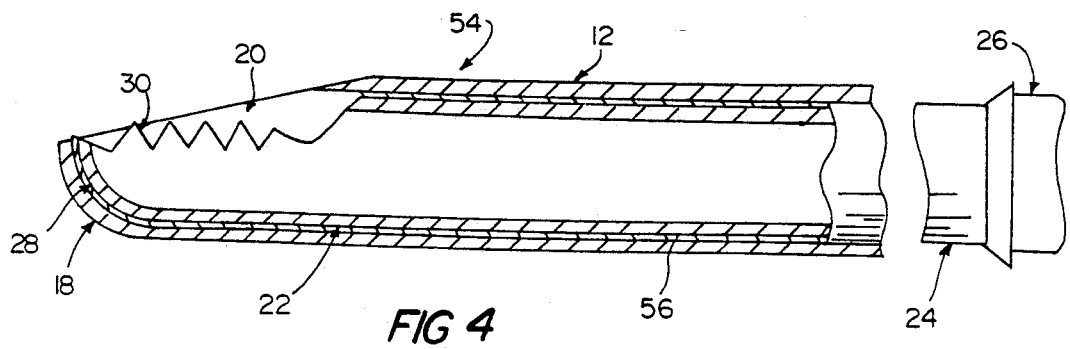
FIG. 4 is a broken, side view, partly in section, of a further modification of a surgical cutting instrument according to the present invention.

Another modification of a surgical cutting instrument according to the present invention is shown in FIG. 4 at 54 and includes outer tubular member 12 made of gall-resistant material in its entirety and an inner elongate tubular member 22 made in its entirety from 300 Series stainless steel concentrically disposed in outer member 12. The outer tubular member 12 has a proximal end (not shown) to be secured in hub 16 and a distal end 18 with an opening 20 defining a cutting port or window for receiving anatomical tissue. The inner tubular member 22 includes a proximal end 24 secured in hub 26 and a distal end 28 with a cutting surface 30 configured to cooperate with the opening 20 to cut tissue. The inner member 22 has a bearing surface thereon extending along the entire or substantially the entire length of the inner tubular member and including an outer case 56 formed by surface hardening the outer diameter surface of the inner member 22. The case 56 extends continuously along the inner member 22 from the proximal end 24 to the distal end 28, and the depth of the case 56 measured radially is at least 33 micrometers with the depth being substantially uniform along the length of the inner member, it being noted that the thickness of the case 56 and the thicknesses of the cylindrical walls of the outer and inner members are greatly exaggerated in FIG. 4. The case 56 preferably has a surface hardness of substantially 1000–1200 HV at a case depth of substantially 33 micrometers. Preferably, the case 56 is formed by infusing carbon into the outer diameter surface of the inner member 22 at temperatures below 380° C. to form a hard, integral, surface layer. A preferred method for forming the case 56 is the Hardcor case hardening process of Hardcor B.V., The Netherlands.

The case 56 forms a bearing surface along the entire length of the inner member 22 that reacts effectively with the outer member 12 made from gall-resistant material to allow the inner and outer members to be disposed with little or no gap between the case 56 and the inner diameter of the outer member 12 while avoiding wear or abrasion, metal flaking, galling and seizure of the surgical instrument and while withstanding high thrust and radial loads.

Figure 5:
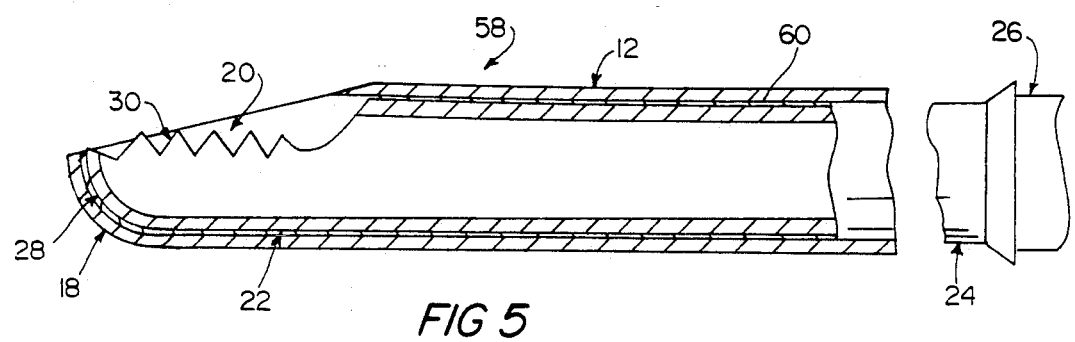
FIG. 5 is a broken, side view, partly in section, of an additional modification of a surgical cutting instrument according to the present invention.

Another modification of a surgical cutting instrument according to the present invention is shown in FIG. 5 at 58 and includes an outer tubular member 12 made of 300 Series stainless steel in its entirety and an inner tubular member 22 made in its entirety from gall-resistant material. The outer tubular member 12 includes a proximal end (not shown) to be secured in hub 16 and a distal end 18 having opening 20 defining a cutting port or window for receiving anatomical tissue. The inner member 22 has a proximal end 24 secured in hub 26 and a distal end 28 with cutting surface 30 for cutting tissue through the opening 20. The inner member 22 has a bearing surface thereon extending the entire or substantially the entire length of the inner tubular member and including a coating 60 of chromium fixed and secured on the inner member 22, the coating 60 extending substantially the entire length of the inner member 22 from the proximal end 24 toward the distal end 28 and terminating proximally of the distal end 28 such that the distal end including the cutting surface 30 remains uncoated. Preferably, the coating 60 is formed on the outer diameter surface of the inner member 22 by electrodeposition, and the distal end 28 including the cutting surface 30 is masked during the coating process to prevent deposition of chromium on the masked area. According to a preferred embodiment, the inner member 22 is masked from the distal end 28 a distance of substantially 0.625 to 0.650 inch proximally of the distal end such that the chromium coating 60 extends continuously on the inner member from the proximal end 24 in a distal direction to substantially 0.625 to 0.650 inch proximally of the distal end 28. It is preferred that the coating 60 have a uniform thickness of substantially 0.0001 to 0.0002 inch such that the outer diameter of the inner member 22 including the coating 60 can be the same, or substantially the same, as the inner diameter of the outer member 12 resulting in minimal or no gap or clearance between the coating 60 and the outer member 12 and only a very small gap at the inner and outer member distal ends, it being noted that the thickness of the coating and the cylindrical walls of the inner and outer members are greatly exaggerated in FIG. 5.

Figure 6:
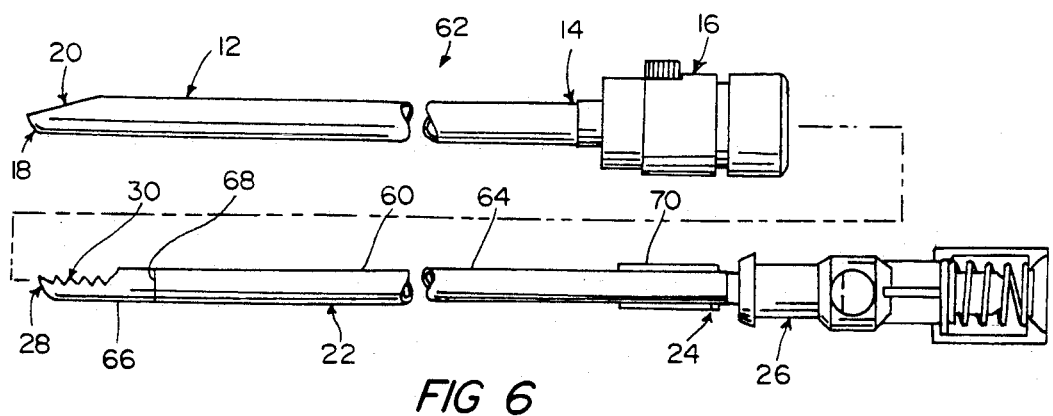
FIG. 6 is an exploded, side view of another modification of a surgical cutting instrument according to the present invention.
Figure 7:
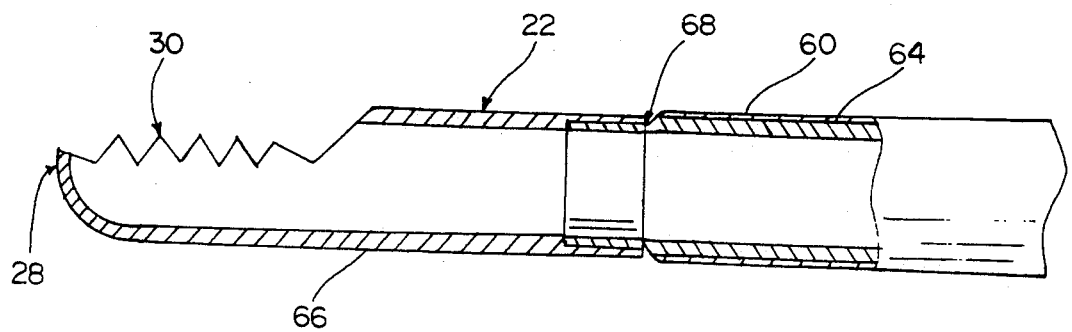
FIG. 7 is a broken, side view, partly in section, of the inner tubular member of the surgical cutting instrument of FIG. 6.

An additional modification of a surgical cutting instrument according to the present invention is shown in FIGS. 6 and 7 at 62 and includes an outer tubular member 12 made from 300 Series stainless steel in its entirety and having a proximal end 14 coupled with the hub 16, and an inner tubular member 22 concentrically, movably disposed within the outer member 12 and having a proximal end 24 coupled with the hub 26. The outer member 12 has a distal end 18 with an opening 20 for receiving tissue. The inner member 22 includes a cylindrical body 64 and a cylindrical distal tip 66 joined to the body 64 at a junction 68. The cylindrical body 64 terminates proximally at proximal end 24, and the tip 66 terminates distally at a distal end 28 with the cutting surface 30 being disposed on the tip 66. The tip 66 is made in its entirety from gall-resistant material, and the cylindrical body 64 is made from 300 Series stainless steel in its entirety. As shown in FIG. 7, wherein only the inner member 22 is shown, a bearing surface including a coating 60 of chromium is fixed and secured on the outer diameter surface of the cylindrical body 64 to extend continuously along the length of the body 64 from the proximal end 24 to the junction 68. It is preferred that the coating 60 be formed on the body 64 by electro-deposition; and, therefore, the tip 66 can be masked during the coating process to prevent deposition of chromium thereon. According to a preferred embodiment, the length of the tip 66 from the junction 68 to the distal end 18 is substantially 0.625 to 0.650 inch. Preferably, the coating 60 has a uniform thickness of 0.0001 to 0.0002 inch, and the inner member 22 is disposed within the outer member 12 with little or no gap between the coating 60 and the inner diameter of the outer member 12, it being noted that the thicknesses of the coating and the cylindrical wall of the inner member are exaggerated in FIG. 7. Preferred methods of joining the body 64 to the tip 66 include brazing and welding. In a preferred embodiment, a bearing 70 is disposed on the inner member 22, as shown in FIG. 6, and includes a sleeve of minimal thickness disposed over the proximal end 24 to be positioned adjacent the proximal end 14 of the outer member 12 when the inner member is concentrically mounted within the outer member. Preferably, the bearing 70 is made from a length of thin-walled, heat shrinkable, industrial tubing, such as TFE (tetrafluoroethylene) heat shrinkable tubing made by Teleflex Incorporated, and is heat-shrunk on to the inner member 22 adjacent the proximal end 24.

The chromium coating 60 and the uncoated, distal tip 66 made from gall-resistant material enable the inner tubular member to be disposed within the outer tubular member with virtually no gap therebetween while avoiding wear or abrasion, metal flaking, galling and seizure during operation wherein the inner tubular member can be rotated within the outer tubular member at speeds of 2500 RPM and greater. The chromium coating 60 forms an elongate bearing surface along substantially the entire length of the inner tubular member for engaging and contacting the inner diameter surface of the outer tubular member as the inner tubular member is moved relative to the outer tubular member. The physical characteristics of the chromium coating, when utilized with the 300 Series stainless steel outer member, produce a favorable chemical reaction that enables the surgical instrument to resist wear due to abrasion, metal flaking, galling and seizure along the length of the surgical instrument when the inner tubular member contacts the outer tubular member. The chromium coating 60 also disburses heat and eliminates localized hot spots along the length of the inner tubular member and resists deformation at high temperatures. Additionally, the chromium coating 60 significantly strengthens the inner tubular member and enables the inner member to withstand significantly greater thrust and radial loads without galling. The gall-resistant material of the distal tip 66 provides even superior bearing characteristics in terms of strength and resistance to abrasion, metal flaking, galling and seizure. The gall-resistant material prevents concentrations of heat at the distal end of the surgical cutting instrument and strengthens the inner member distal end to withstand increased thrust and radial loads. The bearing 70 at the proximal end of the surgical cutting instrument provides additional stability and enables the surgical cutting instrument to withstand increased radial or side loads without damage to and misalignment of the inner and outer members. The gall-resistant material behaves as if it possesses a high surface hardness when utilized with the relatively lower surface hardness of the 300 Series stainless steel outer tubular member, thusly providing excellent bearing properties. The chromium coating 60 and the distal tip 66 dramatically increase the effectiveness of the inner tubular member as a bearing surface in an economically feasible manner while promoting accurate positioning of the inner tubular member within the outer tubular member, eliminating wear, metal flaking, galling and seizure of the surgical cutting instrument, increasing the life and reliability of the surgical cutting instrument, enabling diverse functions to be performed in diverse types of tissue with precision and accuracy, permitting the surgical cutting instrument to perform under extreme load conditions and allowing the inner and outer tubular members to be made from 300 Series stainless steel. Accordingly, easier and smoother precision cutting is accomplished with the surgical cutting instrument of the present invention while tissue is prevented from entering the gap or clearance between the inner and outer tubular members and becoming wrapped around the inner tubular member 22 due to the gap being very small. Moreover, proper alignment of the cutting surface 30 with the opening 20 greatly enhances cutting efficiency by reducing the force required to move the cutting surface 30 past the opening 20 and reduces the time required to conduct various surgical procedures.

Figure 8:
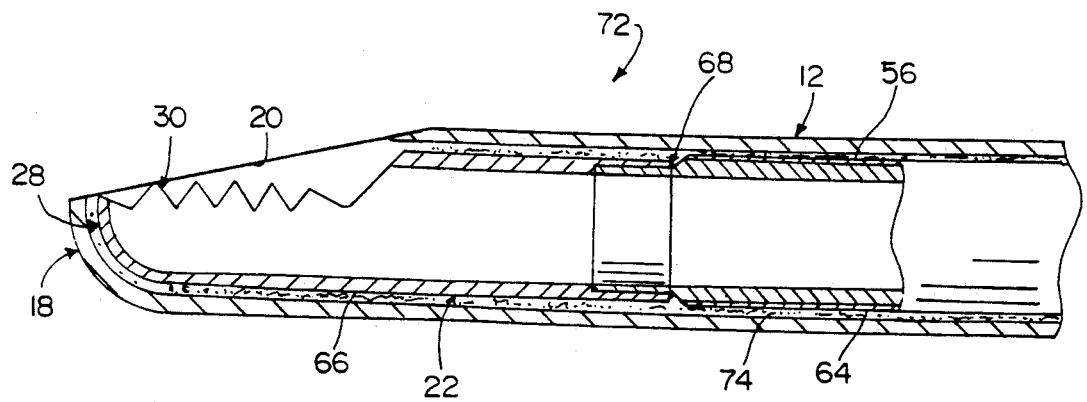
FIG. 8 is a broken, side view, partly in section, of an additional modification of a surgical cutting instrument according to the present invention.

A further modification of a surgical cutting instrument according to the present invention is shown in FIG. 8 at 72, only a distal end of the surgical cutting instrument 72 being shown. The surgical cutting instrument 72 includes an outer tubular member 12 made of 300 Series stainless steel in its entirety and having a proximal end to be coupled with the hub 16 and an inner tubular member 22 disposed concentrically within the outer member 12 and having a proximal end to be coupled with hub 26. The outer member 12 has a distal end 18 with a cutting port or window defined by opening 20. The inner member 22 includes a cylindrical body 64 terminating proximally at proximal end 24 and a cylindrical distal tip 66 joined to the body 64 at a junction 68 and terminating distally at distal end 28, with a cutting surface 30 formed on distal tip 66 for cooperating with the opening 20 at the distal end of the outer tubular member. The body 64 is made from 300 Series stainless steel in its entirety and the distal tip 66 is made from gall-resistant material in its entirety. A bearing surface including an outer case 56 is formed on the body 64 by surface hardening the outer diameter surface thereof, and the case 56 extends continuously along the body 64 from the proximal end to the junction 68. The depth of the case 56 measured radially on the body 64 is at least 33 micrometers with the case depth being substantially uniform along the length of the body 64. Preferably, the surface hardness of the case 56 is substantially 1000-1200 HV at a case depth of substantially 33 micrometers. The length of the distal tip 66 from the distal end 28 to the junction 68 is substantially 0.625 to 0.650 inch. The inner member 22 is concentrically, movably mounted within the outer member 12 with little or no gap between the case 56 and the inner diameter of the outer member 12 and a biocompatible lubricant 74 coating the case 56 is disposed between the outer member and the case 56, it being noted that the size of the gap between the inner and outer members as well as the thicknesses of the case and the cylindrical walls of the inner and outer members are greatly exaggerated in FIG. 8. Preferably, the lubricant 74 is a white, food grade grease, such as NLG1 #2 mineral oil grease with aluminum complex manufactured by Dow Corning, and the coating 74 can extend between the distal tip 66 and the outer member 12. The case 56 forms a bearing surface along substantially the entire length of the inner member 22 that reacts effectively with the 300 Series stainless steel outer member 12 to resist wear due to abrasion, metal flaking, galling and seizure when the inner member is rotated within the outer member and permits the inner member to withstand high thrust and radial loads with the lubricant 74 increasing the wear and galling resistance of the surgical instrument and thusly enhancing cutting precision and efficiency. It will be appreciated that the lubricant 74 can be used between relatively movable, inner and outer tubular members made of stainless steel as well as between the various inner and outer members shown herein.

The surgical cutting instrument according to the present invention allows components of the surgical cutting instrument to be made of stainless steel while resisting wear, abrasion, galling and seizure and maximizing cutting efficiency and precision while allowing the inner tubular member to be mounted within the outer tubular member with virtually no gap therebetween for operation at high speeds. Where the inner or outer member is made from gall-resistant material in its entirety, the other member can be made of 300 Series stainless steel in its entirety with the gall-resistant material serving as a bearing surface along the length of the surgical cutting instrument. Where the outer tubular member is made from gall-resistant material, the inner tubular member can be made from 300 Series stainless steel and provided with a bearing surface such as a surface hardened outer case or a coating or layer of chromium along the entire or substantially the entire length of the inner tubular member to provide superior wear and galling resistant properties. Where the outer tubular member is made from 300 Series stainless steel and the inner tubular member is made from gall-resistant material, a bearing surface such as a chromium coating or a surface hardened outer case can be provided along the entire or substantially the entire length of the inner tubular member. The inner tubular member can be formed of one-piece integral construction, or the inner tubular member can be formed of multiple parts. Where formed of multiple parts, the inner member can include a body made of 300 Series stainless steel in its entirety and a distal tip joined to the body and made of gall-resistant material in its entirety. A bearing surface such as a chromium coating or a surface hardened outer case can be provided along the entire length of the body. A biocompatible lubricant placed between the inner and outer tubular members of the surgical cutting instrument further enhances wear and galling resistance, and a sleeve bearing at the proximal end of the surgical cutting instrument increases the side loading that the surgical cutting instrument can safely withstand.

Having described preferred and alternative embodiments of a new and improved surgical cutting instrument, is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical cutting instrument comprising
an elongate outer tubular member having a distal end, an inner diameter and an opening at said distal end for receiving anatomical tissue;
an elongate inner tubular member disposed within said outer tubular member and having a distal end, an outer diameter and a cutting surface at said distal end for cooperating with said opening to cut tissue, at least said inner member distal end including said cutting surface being made from gall-resistant material in its entirety;
a bearing layer on said inner member extending from said gall-resistant material toward said proximal end; and
means for mounting said inner and outer tubular members for relative movement to position said cutting surface to engage tissue through said opening, said gall-resistant material and said bearing layer together forming a bearing surface along substantially the entire length of the surgical cutting instrument to permit said inner diameter to be substantially the same as said outer diameter.

2. A surgical cutting instrument as recited in claim 1 wherein said bearing layer includes a surface hardened case.

3. A surgical cutting instrument as recited in claim 2 wherein the depth of said case measured radially on said inner tubular member is at least 33 micrometers and said case has a hardness of substantially 1000 to 1200 HV at a depth of 33 micrometers.

4. A surgical cutting instrument as recited in claim 3 wherein said case includes carbon infused into said inner tubular member.

5. A surgical cutting instrument as recited in claim 1 wherein said bearing layer includes a coating of chromium along said outer diameter.

6. A surgical cutting instrument as recited in claim 5 wherein the depth of said coating measured radially on said inner tubular member is substantially 0.0001 to 0.0002 inch.

7. A surgical cutting instrument as recited in claim 6 wherein said coating is formed by electrodeposition.

8. A surgical cutting instrument as recited in claim 1 wherein said gall-resistant material includes a gall-resistant, austenitic stainless steel alloy.

9. A surgical cutting instrument as recited in claim 1 wherein said inner and outer tubular members each include a proximal end and said means for mounting includes a handpiece receiving said proximal ends.

10. A surgical cutting instrument as recited in claim 1 wherein a gap is disposed between said inner diameter and said outer diameter and the width of said gap measured radially with said inner and outer tubular members is substantially 0.00075 inch or less.

11. A surgical cutting instrument comprising
an elongate outer tubular member having a distal end, a proximal end and an opening at said distal end for receiving anatomical tissue;
an elongate inner tubular member having a cylindrical body, a cylindrical tip joined to said body, a distal end on said tip, a proximal end on said body and a cutting surface on said tip for engaging anatomical tissue, said inner tubular member being disposed within said outer tubular member to permit relative movement between said inner and outer tubular members to position said cutting surface to engage tissue through said opening, said distal end and tip being formed of gall-resistant material in its entirety and said body being formed of 300 Series stainless steel in its entirety; and an elongate bearing surface secured on said body and extending from said distal tip toward said proximal end substantially the entire length of said inner tubular member.

12. A surgical cutting instrument as recited in claim 11 wherein said bearing surface includes a coating of chromium on the outer diameter of said body.

13. A surgical cutting instrument as recited in claim 12 wherein the depth of said coating measured radially on said body is substantially 0.0001 to 0.0002 inch.

14. A surgical cutting instrument as recited in claim 13 wherein said coating is formed on said body by electrodeposition.

15. A surgical cutting instrument as recited in claim 11 wherein said bearing surface includes a hardened case on the outer diameter of said body.

16. A surgical cutting instrument as recited in claim 15 wherein the depth of said case measured radially on said body is at least 33 micrometers and said case has a hardness of substantially 1000 to 1200 HV at a depth of 33 micrometers.

17. A surgical cutting instrument as recited in claim 16 wherein said case includes carbon infused into said inner tubular member.

18. A surgical cutting instrument as recited in claim 17 further including a lubricant coating on said case.

19. A surgical cutting instrument as recited in claim 11 wherein said distal tip is joined to said body at a weld junction.

20. A surgical cutting instrument as recited in claim 11 wherein said distal tip is joined to said body at a brazing junction.

21. A surgical cutting instrument comprising an elongate outer tubular member having a distal end, a proximal end and an opening at said distal end for receiving anatomical tissue;

an elongate inner tubular member having a cylindrical body, a cylindrical tip joined to said body, a distal end on said tip, a proximal end on said body and a cutting surface on said tip for engaging anatomical tissue, said inner tubular member being disposed within said outer tubular member to permit relative movement between said inner and outer tubular members to position said cutting surface to engage tissue through said opening, said tip being formed of gall-resistant material in its entirety and said body being formed of 300 Series stainless steel in its entirety;

an elongate bearing surface secured on said body and extending from said distal tip toward said proximal end substantially the entire length of said inner tubular member; and a sleeve bearing disposed on said inner member.

22. A surgical cutting instrument as recited in claim 21 wherein said sleeve bearing includes a length of thin-walled tubing heat-shrunk on said inner tubular member.

23. A surgical cutting instrument as recited in claim 15 wherein said tubing is made from tetrafluoroethylene.

24. A surgical cutting instrument as recited in claim 23 wherein said sleeve bearing is disposed on said inner tubular member proximal end.

25. A surgical cutting instrument comprising an elongate outer tubular member having a distal end, a proximal end and an opening at said distal end for receiving anatomical tissue;

an elongate inner tubular member having a cylindrical body, a cylindrical tip joined to said body at a junction, a distal end on said tip, a proximal end on said body and cutting surface on said tip for engaging anatomical tissue, said distal tip having a length from said distal end to said junction of substantially 0.625 to 0.650 inch, said inner tubular member being disposed within said outer tubular member to permit relative movement between said inner and outer tubular members to position said cutting surface to engage tissue through said opening, said tip being formed of gall-resistant material in its entirety and said body being formed of 300 Series stainless steel in its entirety;

an elongate bearing surface secured on said body and extending from said distal tip toward said proximal end substantially the entire length of said inner tubular member.

26. A surgical cutting instrument comprising an outer elongate tubular member having a distal end and a cutting port at said distal end for receiving anatomical tissue;

an inner tubular member having a distal end and a cutting surface at said distal end for engaging tissue in said cutting port, said inner tubular member being mounted in said outer tubular member to permit relative movement between said inner and outer tubular members to allow said cutting surface to engage tissue in the cutting port, the outer diameter of said inner tubular member being substantially the same as the inner diameter of said outer tubular member; and a biocompatible lubricant disposed between said inner and outer tubular members, said lubricant including a white, food-grade grease.

27. A surgical cutting instrument as recited in claim 34 and further including an elongate bearing surface disposed on one of said inner and outer tubular members extending substantially the entire length of the surgical cutting instrument and wherein said lubricant is disposed between said bearing surface and the other of said inner and outer tubular members.

28. A surgical cutting instrument comprising an outer elongate tubular member having a distal end and a cutting port at said distal end for receiving anatomical tissue;

an inner tubular member having a distal end and a cutting surface at said distal end for engaging tissue in said cutting port, said inner tubular member being mounted in said outer tubular member to permit relative movement between said inner and outer tubular members to allow said cutting surface to engage tissue in the cutting port, the outer diameter of said inner tubular member being substantially the same as the inner diameter of said outer tubular member; and a biocompatible grease lubricant disposed between said inner and outer tubular members.

* * * * *